(12) United States Patent
Ben et al.

(10) Patent No.: US 8,728,533 B2
(45) Date of Patent: May 20, 2014

(54) COMPOSITION COMPRISING CRUSTACEAN GASTROLITH COMPONENTS AND ITS USE

(71) Applicants: Ben-Gurion University of the Negev Research and Development Authority, Beer-Sheva (IL); Yossi Ben, D.N. Arava (IL)

(72) Inventors: Yossi Ben, D.N. Arava (IL); Amir Sagi, Omer (IL)

(73) Assignees: Yossi Ben, D.N. Arava (IL); Ben-Gurion University of the Negev Research and Development Authority, Beer-Sheva (IL)

(*) Notice: Subject to any disclaimer, the term of this patent is extended or adjusted under 35 U.S.C. 154(b) by 0 days.

(21) Appl. No.: 13/728,508

(22) Filed: Dec. 27, 2012

(65) Prior Publication Data
US 2013/0122117 A1    May 16, 2013

Related U.S. Application Data

(63) Continuation of application No. 12/443,987, filed as application No. PCT/IL2007/001211 on Oct. 7, 2007.

(30) Foreign Application Priority Data

Oct. 5, 2006 (IL) .......................................... 178495

(51) Int. Cl.
*A61K 35/64* (2006.01)

(52) U.S. Cl.
USPC ........................................................ 424/538

(58) Field of Classification Search
USPC .................................................. 424/530, 538
See application file for complete search history.

(56) References Cited

U.S. PATENT DOCUMENTS

| | | | | |
|---|---|---|---|---|
| 4,199,496 A * | 4/1980 | Peniston et al. | ............... | 530/400 |
| 4,237,147 A | 12/1980 | Merten | | |
| 5,886,012 A * | 3/1999 | Pang et al. | ..................... | 514/356 |
| 2003/0077604 A1* | 4/2003 | Sun et al. | .......................... | 435/6 |
| 2004/0028748 A1 | 2/2004 | Sasaya | | |
| 2004/0234614 A1* | 11/2004 | Strong | .......................... | 424/493 |
| 2006/0165784 A1 | 7/2006 | Zhao | | |

FOREIGN PATENT DOCUMENTS

| | | | | |
|---|---|---|---|---|
| EP | 1666046 | * | 6/2006 | ......... A61K 31/7008 |
| JP | 2004081739 | | 3/2004 | |
| WO | WO2005025581 | * | 3/2005 | ......... A61K 31/7008 |
| WO | 2005115414 | | 12/2005 | |
| WO | 2006043966 | | 4/2006 | |

OTHER PUBLICATIONS

Melanoma skin cancer. American Cancer Society. 2013.*
Non-Hodgkin lymphoma. American Cancer Society. 2012.*
Spiegel et al. Group therapy and hypnosis reduce metastatic breast carcinoma pain. Psychosomatic Medicine. 1983;45(4):333-339.*
Addadi, L. et al., (2003) Taking advantage of disorder: amorphous calcium carbonate and its roles in biomineralization. Advanced Materials 15(12):959-970.
Akiva-Tal, Anat et al., (2011) In situ molecular NMR picture of bioavailable calcium stabilized as amorphous CaCO3 biomineral in crayfish gastroliths. Proc Natl Acad Sci USA 108(36):14763-14768.
Bajpai, Anurag et al., (2004) Pseudohypoparathyroidism Presenting with Bony Deformities Resembling Rickets. Indian Journal of Pediatrics 71(4):345-347.
Chick, Leland R. and Borah, Gregory (1990) Calcium carbonate gel therapy for hydrofluoric acid burns of the hand. Plastic and Reconstructive Surgery 86(5):935-940.
Database WPI Week 200432 Thomson Scientific, London, GB; AN 343036 XP002512142 & JP 2004 081739 A (Bankoku Needle MFG) Mar. 18, 2004 & JP 2004 081739 A (Akashi Mitsuru; Tabata Masashi; Biomedical Technology Hybrid L) Mar. 18, 2004.
Hu, Y.-Y. et al., (2010) Strongly bound citrate stabilizes the apatite nanocrystals in bone. Proc Natl Acad Sci USA 107(52):22425-22429.
Huxley T. H. "The Crayfish : An Introduction to the Study of Zoology" Chapter 1, 1879.
Johnsson, M. et al., (1991) Adsorption and mineralization effects of citrate and phosphocitrate on hydroxyapatite. Calcif Tissue Int 49(2):134-137.
Lee, Hyun Sook et al., (2005) Fabrication of unusually stable amorphous calcium carbonate in an ethanol medium. Materials Chemistry and Physics 93(2-3):376-382.
Loste, Eva et al., (2003) The role of magnesium in stabilising amorphous calcium carbonate and controlling calcite morphologies. Journal of Crystal Growth 254(1-2):206-218.
Malkaj, P. and Dalas, E. (2007) The effect of acetaminophen on the crystal growth of calcium carbonate. J Mater Sci Mater Med 18(5):871-875.
Manoli, F. and Dalas, E. (2002) The effect of sodium alginate on the crystal growth of calcium carbonate. J Mater Sci Mater Med 13(2):155-158.
Martins, Manuel A. et al., (2008) Hydroxyapatite micro- and nanoparticles: nucleation and growth mechanisms in the presence of citrate species. J Colloid Interface Sci 318(2):210-216.
Maruyama, Koji et al., (2011) Synthesizing a composite material of amorphous calcium carbonate and aspartic acid. Materials Letters 65(2):179-181.
Merck manual of diagnosis and therapy 17th edition 1999 pp. 1979,1982.

(Continued)

*Primary Examiner* — Ruth Davis
*Assistant Examiner* — Lynn Y Fan
(74) *Attorney, Agent, or Firm* — Roach Brown McCarthy & Gruber, P.C.; Kevin D. McCarthy

(57) ABSTRACT

Provided is a formulation containing amorphous or microcrystalline calcium carbonate finely interspersed with organic matter in a ratio of 10 parts of the carbonate per 1 to 3 parts of the organic matter, wherein the organic matter consists of chitin and polypeptide. The formulation is efficient in treating various pathological conditions, including proliferative diseases, neurological disorders, and musculoskeletal disorders.

18 Claims, No Drawings

(56) References Cited

OTHER PUBLICATIONS

Oculi cancrorum: very proper for falls and a pleurisy Ann R Coll Surg Engl. Jan. 1957;20(1):57-8.

OsteoPhase. Tango advanced Nutrition—Healthy Bone Support Formula 2011.

Osteoporosis: How to strengthen your bones and prevent fractures. The healthier Life. 2005.

Reddi, A. H. et al., (1980) Influence of phosphocitrate, a potent inhibitor of hydroxyapatite crystal growth, on mineralization of cartilage and bone. Biochem Biophys Res Commun 97(1):154-159.

Rodriguez-Blanco, J. D. et al., (2012) The role of pH and Mg on the stability and crystallization of amorphous calcium carbonate. Journal of Alloys and Compounds 536(Supp 1):S477-S479 International Symposium on Metastable, Amorphous and Nanostructured Materials, ISMANAM-2011 (Jun. 26 to Jul. 1, 2011).

Schneiders, Wolfgang et al., (2007) Effect of modification of hydroxyapatite/collagen composites with sodium citrate, phosphoserine, phosphoserine/RGD-peptide and calcium carbonate on bone remodelling. Bone 40 (4).1048-1059.

Thomas, N. L. and Birchall, J. D. (1983) The retarding action of sugars on cement hydration. Cement and Concrete Research 13(6):830-842.

Thys-Jacobs, Susan et al., (1998) Calcium carbonate and the premenstrual syndrome: Effects on premenstrual and menstrual symptoms. American Journal of Obstetrics and Gynecology 179(2):444-452.

* cited by examiner

COMPOSITION COMPRISING CRUSTACEAN GASTROLITH COMPONENTS AND ITS USE

REFERENCE TO CO-PENDING APPLICATIONS

Priority is a continuation of U.S. patent application Ser. No. 12/443,987 having a filing date of Oct. 7, 2007; which is a 371 of international application PCT/IL2007/001211, filed on Oct. 7, 2007; which claims priority from Israeli patent application no. 178495, filed on Oct. 5, 2006.

FIELD OF THE INVENTION

The present invention relates to a composition of matter comprising calcium carbonate dispersed finely with organic matter consisting essentially of chitin and polypeptide. Pharmaceutical uses of said composition of matter are provided.

BACKGROUND OF THE INVENTION

It has long been recognized that absorption and bioavailability of orally delivered drugs and nutrients are affected by other co-delivered components. Some effects may seem obvious, such as binding of metals in chelates, but chemical and biological interactions among the components, comprising original components and the components joining the interplay in the body, are often too complex to allow explanations or predictions of the observed phenomena. Metabolic, hormonal, and immunological processes may be influenced by both chemical composition and physical state of the delivered materials.

It has been, for example, shown that high doses of calcium do not necessarily slow bone loss. In fact, some populations with high intakes of calcium also have high rates of osteoporosis, supposedly due to an effect of high protein intake, whereas some African cultures consume no dairy products and typically get only 175 to 475 milligrams of calcium per day (800 mg is the U.S. RDA), but they have low rates of osteoporosis.

WO 2005/115414 disclosed an orally-administrable composition comprising stable amorphous calcium carbonate and its use in treating bone disorders. The present invention aims at a composition of matter comprising calcium carbonate dispersed in a lesser part of organic matter consisting of chitin and polypeptide.

It is another object of this invention to provide pharmaceutical compositions comprising calcium carbonate dispersed in a lesser part of organic matter consisting of chitin and polypeptide.

Other objects and advantages of present invention will appear as description proceeds.

SUMMARY OF THE INVENTION

The present invention provides a composition of matter, comprising 100 weight parts (wp) of calcium carbonate mixed finely with from 10 to 30 wp of organic matter comprising from 90 to 99 wt % chitin and from 1 to 10 wt % polypeptide. Said composition of matter, may further comprise up to 40 wp of inorganic salts other than calcium carbonate ($CaCO_3$) and up to 30 wp of moisture per 100 wp of $CaCO_3$. In one preferred embodiment of the invention, said composition of matter originates from crustacean gastrolith. In another preferred embodiment of the invention, said composition of matter originates from artificial mixture of $CaCO_3$, chitin, and polypeptide (Pp). Said composition preferably comprises 100 wp of $CaCO_3$ and from 15 to 25 wp of organic matter essentially consisting of chitin and polypeptide, which organic matter comprises from about 95 to 99 wt % chitin and from 1 to 5 wt % polypeptide. Said other salts are preferably selected from salts comprising magnesium, calcium, potassium, strontium, sodium, phosphate, sulfate, carbonate, chloride, bromide, and fluoride, of course with the proviso that said salts do not simultaneously comprise calcium and carbonate, so as not to increase the desired calcium carbonate amount.

The invention is further directed to a pharmaceutical formulation for oral administration comprising the composition of matter described above. Said pharmaceutical formulation comprises calcium carbonate ($CaCO_3$) finely mixed with an organic matter essentially consisting of chitin and polypeptide (Pp), wherein said organic matter and said $CaCO_3$ are present in a ratio of from 1/10 to 3/10, and said Pp and said chitin are present in a ratio of from 1/100 to 1/10, for treating conditions associated with calcium metabolism or calcium signaling. In a preferred embodiment, said pharmaceutical formulation originates from crustacean gastrolith. In another preferred embodiment, said pharmaceutical formulation originates from artificial mixture of $CaCO_3$, chitin, and Pp. Said pharmaceutical formulation comprises $CaCO_3$ finely dispersed or mixed with an organic matter (Om) essentially consisting of chitin and Pp, wherein said organic matter and said $CaCO_3$ are present in a ratio of from 1/10 to 3/10, and said Pp and chitin are present in a ratio of from 1/100 to 1/10, for treating conditions selected from the group consisting of pain, proliferative diseases, neurological disorders, immunologic disorders, cardiovascular diseases, pulmonary diseases, nutritional disorders, reproductive disorders, musculoskeletal disorders, and dental problems. Said treating may comprise mitigating the symptoms of the diseases. Said proliferative disease is selected from sarcomas, carcinomas, lymphomas and melanomas. Said carcinoma is preferably breast carcinoma or bronchogenic carcinoma. Said treating may comprise shrinking tumors, stopping their growth, or slowing down or inhibiting the cell proliferation in the tumors. Said pain may be selected from postoperative pain, pain after injury, pain associated with cancer, and neuropathic pain. Said neurologic disorder may be selected from demyelinating diseases, dementias, and movement disorders; said disorders being, for example, multiple sclerosis, Alzheimer's disease, Parkinson's disease, or other degenerative disease. Said condition may comprise a bone or bone marrow disorder, such as fracture or osteoporosis. In a preferred embodiment, a composition of the invention is used for treating a neurodegenerative disorder.

The invention relates to the use of a composition of matter according to the invention as a medicament. The invention also relates to the use of the composition of matter in the manufacture of a medicament for treating cancer, or neurodegenerative disorders, or bone disorders and injuries.

Provided is a novel method of treating cancer, comprising orally administering a composition of matter containing an organic matter finely mixed with $CaCO_3$, said organic matter essentially consisting of chitin and Pp, wherein said organic matter and $CaCO_3$ are present in a ratio of from 1/10 to 3/10, and wherein said Pp and chitin are present in a ratio of from 1/100 to 1/10. Provided is also a novel method of treating a degenerative disorder, comprising orally administering a composition of matter containing an organic matter finely mixed with $CaCO_3$, said organic matter essentially consisting of chitin and Pp, wherein said organic matter and $CaCO_3$ are present in a ratio of from 1/10 to 3/10, and wherein said Pp and chitin are present in a ratio of from 1/100 to 1/10. Further a method for managing pain is provided, comprising orally administering a composition of matter containing an organic matter (Om) finely mixed with $CaCO_3$, said Om essentially consisting of chitin and Pp, wherein said organic matter and $CaCO_3$ are present in a ratio of from 1/10 to 3/10, and wherein said Pp and chitin are present in a ratio of from 1/100 to 1/10, preferably from 1/100 to 1/20. Finally, a method for treating a bone disorder or injury is provided, comprising orally administering a composition of matter containing an organic matter finely mixed with $CaCO_3$, said organic matter essentially consisting of chitin and Pp, wherein said organic matter and $CaCO_3$ are present in a ratio of from 1/10 to 3/10, and wherein said Pp and chitin are present in a ratio of from 1/100 to 1/10. In said methods of managing pain and of treating cancer, degenerative disorders, bone disorders and injuries, said composition according to the invention is administered orally in daily doses of from about 0.5 to about 5 g.

The invention is directed to a method of preparing the composition of matter comprising 100 weight parts (wp) of calcium carbonate mixed finely with from 10 to 30 wp of organic matter comprising from 90 to 99 wt % chitin and from 1 to 10 wt % polypeptide, which method comprises i) providing a material containing $CaCO_3$ and organic matter (Om), wherein the mass ratio $Om/CaCO_3$ is between 1/10 and 3/10, and wherein said Om consists essentially of chitin and Pp, the mass ratio Pp/chitin being between 1/100 and 1/10; ii) homogenizing the mixture if necessary, and iii) adjusting water content in the mixture to be from 10 to 30 wp per 100 wp $CaCO_3$. In a preferred embodiment of the invention, said material containing $CaCO_3$ and Om in above step i) is obtained from biological source. In another embodiment, said material containing $CaCO_3$ and Om in step i) is an artificial mixture of the components. Said biological source may be an organ or a body part of a crustacean, preferably selected from decapods. Said method of the invention, comprises the steps of i) providing a material containing $CaCO_3$, and Om consisting essentially of chitin and Pp, wherein the mass ratio $Om/CaCO_3$ is between 1/10 and 3/10, and the mass ratio Pp/chitin is between 1/100 and 1/10; optionally adjusting water content in the mixture up to 30 wp per 100 wp $CaCO_3$; iii) optionally adjusting the content of inorganic salts other than $CaCO_3$ in the mixture up to 40 wp per 100 wp of $CaCO_3$; and iv) homogenizing the mixture to obtain a fine dispersion. Said embodiment employing a biological source may comprise the steps of i) selecting crayfish, monitoring and optionally inducing the formation of gastrolith; harvesting developed gastroliths; iii) drying said gastroliths in hot air until only about 20 parts of water per 100 parts of $CaCO_3$ is retained; and iv) grinding said dried gastroliths. Said embodiment employing an artificial mixture, may comprise, in one possible procedure but without being limited to it, the steps of i) dispersing calcium hydroxide in water; ii) optionally admixing sodium and/or potassium phosphate; iii) saturating the dispersion with carbon dioxide while adding chitin and polypeptide; iv) centrifuging the suspension; v) discarding a part of the supernatant; and vi) drying the part of the dispersion containing the sediment until only about 20 parts of water per 100 parts of $CaCO_3$ is retained.

DETAILED DESCRIPTION OF THE INVENTION

It has now been found that a composition of matter, comprising 100 weight parts (wp) of calcium carbonate mixed with about 20 wp of organic matter consisting of chitin and a lesser amount of polypeptide, when orally administered to patients suffering from proliferative or neurodegenerative diseases, has a surprisingly positive effect on the course of the disease. Particularly, a composition originating from crustacean gastrolith, comprising per 100 wp of calcium carbonate about 20 wp of organic matter consisting of chitin and polypeptide, and which further contained about 30 wp of additional inorganic salts and 20 wp of moisture, exhibited healing or mitigating effects in the patients with proliferative disorders. For example, in the trials comprising advanced cancer cases, a daily dose of 1.5 g of the above said gastrolith-based composition led to dramatic effects on the patients' state. Within several days, the pain decrease was reported by the patients, and in continued treatments, the changes included improved blood tests and remissions of the metastatic tumors. In other trials, patients suffering from advanced Alzheimer's disease (AD) exhibited improvements when being daily administered around 1 g of the said composition, wherein the benign effects included improved cognitive abilities and increased physical activity, and further included mitigation effects on the patients suffering from chronic pains, particularly bone pains.

The composition of matter according to the invention has been found to mitigate pains in a diverse group of conditions, comprising bone weakening and injuries, the subjectively improved state of the patients being accompanied by impressive laboratory findings. In a diverse group of cases comprising conditions associated with wounded or weakened bones, daily doses of about 0.8 to 1.5 g of a composition according to the invention administered during experimental periods of from days to months accelerated healing of bone fractures, and generally improved laboratory tests, the observed effects including, e.g., increased bone density in osteoporosis.

The invention thus relates to a composition of matter comprising 100 weight parts (wp) of calcium carbonate mixed with from 10 to 30 wp of organic matter consisting of chitin and polypeptide, and to the use of said composition in managing chronic pain and in treating conditions comprising chronic pain. Amazingly, while alleviating the pain, the composition of the invention additionally contributes to healing the underlying causative factor, such as a proliferative disease, or to mitigating the accompanying main disorder, such as Alzheimer disease. When trying to understand such unexpected effects, an important role of calcium in the regulation of all bodily functions must be taken into consideration. Calcium forms up to 5% of the solids in the human body, and beside structural functions in the bones, it has many important regulatory and signaling functions, as indicated by, in view of its total amount incredibly low, intracellular calcium ion concentrations of about $10^{-7}$ M. Calcium ions, being an intracellular signal transducer, participate in controlling muscle contraction, releasing neurotransmitters, secreting hormones, regulating cell motility and mitosis, and affecting gene expression. Calcium signaling stands at the beginning of the life when participating at the egg fertilization, and it stands at its end when the cells die of apoptotic death.

No wonder, that calcium is implicated in many disorders, even if the pathogenesis is obscure. For example, analyses of brain tissue from AD patients suggested that alterations in cellular calcium homeostasis are associated with the neurodegenerative process. In view of the immense role calcium plays, no simple explanation of all the effects observed after its oral administration can be given, especially when administered together with other components. As mentioned above, both chemical and physical state of an orally administered material may affect the results; calcium carbonate is a quickly available form of calcium, in view of acidic stomach environment, especially when amorphous carbonate is provided, such as carbonate originating from crustacean gastroliths. Furthermore, in a composition of the invention, there are from 10 to 30 weight parts of chitin and polypeptide per 100 weight parts of calcium carbonate, and it can be hardly assessed how the finely admixed organic component affects the behavior of administered calcium. As the components originating from the composition of the invention travel through the alimentary tract, chitin and protein molecules may exhibit occlusive effects on amorphous micro particles or on microcrystals of calcium carbonate, or they may show chelating effects, and the types of eventual interactions will change also according to the changing pH and the presence of digestion factors along the tract, wherein various materials may possibly bind calcium ions, including, for example, bile acids, proteins originating from the administered composition, proteins originating in the body, etc. Furthermore, while attempting to understand the broad effects of the apparently so simple compositions of the invention, the role of the organic macromolecules in finely dispersing the calcium carbonate particles must be taken into account. Chitin may have additional effects, as indicated in various reports showing biological activities of chitin, an example being US 2004/0234614, which describes an immunomodulating effect of inhaled chitin particles. Therefore, without committing themselves to any particular theory, the inventors believe that surprising benign activity of the composition according to the invention may result from concurrent effects of the fine dispersion of inorganic calcium and organic macromolecules, of the mixture of chitin and polypeptide molecules interspersed with amorphous or microcrystalline calcium carbonate, and of the consistence of chitin interwoven in an inorganic/organic web of calcium carbonate with polypeptide. There may be other factors contributing to the final effects of the materials of the invention, but, however theoretically interesting they are, the mutual interactions of the components, their description, or the involved mechanisms are, of course, not a part of the invention.

The composition of matter according to the invention comprises calcium carbonate homogeneously mixed, and finely dispersed, with an organic matter consisting of chitin and polypeptide. If not specified otherwise, whenever the term "calcium carbonate" ($CaCO_3$) is used in the specification, the intended meaning is a finely dispersed material of $CaCO_3$ or a fine particular $CaCO_3$ material; whenever the term "chitin" is used, the intended meaning is an oligosaccharide or polysaccharide of any origin comprising [1-4]-β-linked N-acetyl-D-glucosamine; whenever the term "protein" or "polypeptide" is used in connection with the composition of the invention, the intended meaning is any polypeptide or any mixture of polypeptides that is pharmaceutically acceptable for oral administration. When relating to fine mixing, such homogenization is meant, which provides a mixture in which the original components are mixed down to the level of nanoparticles. The terms "water" and "moisture" are used interchangeably when relating to the composition of matter of the invention. Said organic matter in the composition of matter according to the invention comprises chitin and polypeptide in a total amount of from 10 to 30 weight parts per 100 weight parts of calcium carbonate, and in a ratio of polypeptide/chitin of from 0.01 to 0.1, preferably said total amount is from 15 to 25 wp, and said ratio is from 0.01 to 0.05. The composition of matter according to the invention may further comprise inorganic salts other than calcium carbonate in an amount of up to 40 wp per 100 wp of calcium carbonate, and moisture in an amount of up to 30 wp per 100 wp of calcium carbonate.

The invention is also directed to a pharmaceutical formulation comprising a composition of matter defined above. The pharmaceutical formulation of the invention comprises $CaCO_3$, chitin and polypeptide in a total amount of from 10 to 30 wp per 100 wp of said $CaCO_3$, water up to 30 wt per 100 wp, and may further comprise additional inorganic salts, as well as components used in pharmaceutical formulations to provide a desired consistency, such as a carrier, binding agent, or diluent, provided that the component is inert and in no way affects the chemical or physical properties of the active components that are relevant for their therapeutic activities. For the sake of brevity, the above mentioned components intended to provide a desired consistency to the pharmaceutical formulation are herein called "a filler" or "filler". In a preferred embodiment, a composition of matter according to the invention is pressed into tablets without any filler. Optionally, additional pharmaceutically active agent may be present in a formulation according to the invention, for specific indications, wherein said additional agent may be selected, for example, from antiviral, antifungal, antibacterial, antiseptic, anti-inflammatory or immunomodulatory, antineoplastic, and analgesic agents.

The invention provides a composition of matter comprising $CaCO_3$ finely mixed with chitin and polypeptide for use as a pharmaceutical. The ratio of the organic matter to calcium carbonate in said composition of matter is between 10 to 30 wp organic matter per 100 wp $CaCO_3$, wherein said composition of matter comprises water up to 30 wt per 100 wp $CaCO_3$, and may further comprise additional inorganic salts up to 40 wp per 100 wp of $CaCO_3$.

In one aspect, the invention provides a composition of matter for treating a proliferative disease selected from sarcomas, carcinomas, lymphomas and melanomas. For example, the current treatments available for bronchogenic carcinoma include surgery, radiation therapy, and chemotherapy. While being the leading cause of cancer death among men (32%) and women (25%) [The Merck Manual of Diagnosis and Therapy, $17^{th}$ Ed., 1999], the said condition has a poor prognosis, and a really urgent need is felt for additional treatments which would improve the prospects, or, at least, mitigate the most distressing symptoms, including pains. Frequently found symptoms comprise bone pains. Cancer pain syndromes may be caused by tumors invading bone or soft tissues, compressing or infiltrating nerves, or obstructing a hollow viscus, or they may follow therapy. The composition of matter according to the invention was demonstrated to improve the state of patients with lung cancer. Furthermore, the composition according to the invention was found to mitigate bone pain associated with the proliferative diseases. Particularly a composition originating from crustacean gastrolith, comprising $CaCO_3$ finely mixed with chitin and polypeptide, wherein the ratio of the organic matter to calcium carbonate in said composition was about 20 wp of the organic matter per 100 wp $CaCO_3$, said matter consisting essentially of chitin and protein and further containing about 30 wp of inorganic salts and about 20 wp of moisture per 100 wp $CaCO_3$, was found to cause tumors shrinkage at a daily dose of 0.5-2.0 g.

Among the most frequently occurring proliferative diseases there are breast carcinomas, afflicting one woman in eight. Although showing a better prognosis than lung cancer, many complications frequently appear, including drug toxicity and adverse effects, wherein some women do not respond to standard therapies. Again, the treatment may include surgery, radiation therapy, and chemotherapy, eventually accompanied by endocrine therapy. However, breast cancers require that more treatment elements be simultaneously or subsequently employed. When, for example, including chemotherapy, combination regimens should be used. In any case, palliative treatment is usually necessary, as well as treatments of secondary problems, which problems may comprise trauma, intoxication, post-radiation symptoms, secondary infections, etc. If metastases develop, the current treatments offer an increase of median survival only by 3 to 6 months. The need of new drugs is felt [The Merck Index, Ibid., page 1982]. A composition of matter according to the invention was demonstrated to improve the state of patients with breast cancer metastasized to other organs, wherein the improvements included shrinkage of the tumors, increase of the bone mass, renewal of nail growth after the radiation therapy, improved laboratory blood values. Particularly, a composition of matter according to the invention originating from crustacean gastrolith, comprising $CaCO_3$ finely mixed with chitin and polypeptide, wherein the ratio of the organic matter to calcium carbonate in said composition was about 20 wp of the organic matter per 100 wp $CaCO_3$, said matter consisting essentially of chitin and protein and further containing about 20 wp water about 30 wp inorganic salts per 100 wp $CaCO_3$, was shown to be very effective in amounts up to 2.0 g daily. Importantly, the administration of a composition of the invention surprisingly affects simultaneously a variety of diagnostic parameters and symptoms, including the pain—which is alleviated. The current treatments are strongly invasive, and often lead to trauma and even injury, such as, for example, rib fractures in some patients after radiation therapy [Ibid., page 1979], and the composition of the invention may amazingly contribute even in these cases, since it promotes bone healing. Furthermore, since the composition of the invention was found to have palliative effects, and especially alleviating effects on bone pains, in a variety of disorders, it will be very helpful also in the complex treatments of breast cancers, in which many analgesics have adverse effects, and some are inefficient.

In another aspect of the invention, a composition of matter is provided for treating a neurological disorder, such as pain, and dementia or other neurodegenerative disorders. An example of dementia is Alzheimer disease, of which occurrence above the age of 60 increases nearly linearly with the increasing age, accounting for more than 65% of the dementias in the elderly [Ibid.]. No effective treatments are known against the disease that gradually destroys cognitive functions and finally leads to severe complications and restrictions in physical activities. The composition of matter according to the invention, comprising $CaCO_3$ dispersed in an organic matter consisting essentially of chitin and polypeptide, wherein the ratio of the organic matter to calcium carbonate in said composition is between 10 and 30 wp of the organic matter per 100 wp $CaCO_3$ was found to mitigate the symptoms of Alzheimer's disease. Particularly, a composition originating from crustacean gastrolith, comprising $CaCO_3$ finely mixed with organic matter consisting essentially of chitin and polypeptide, wherein the ratio of the organic matter to calcium carbonate in said composition was about 20 wp of the organic matter per 100 wp $CaCO_3$, and further containing about 20 wp water and about 30 wp inorganic salts per 100 wp $CaCO_3$, was found to mitigate the symptoms of Alzheimer's disease in patients who were administered a daily dose of from 0.8 to 1.5 g, the benign effects including improved cognitive abilities and increased physical activity; and, importantly, in patients with chronic pains, palliative effects of said composition was observed.

Neurological disorders include pain. Pain is sometimes a symptom of a well defined underlying disease or cause, such as cancer or postoperative pain, and sometimes it is a problem occurring without a clear reason, such as neuropathic pain. Chronic pain may develop, for example, after injury. The existing treatments include administration of analgesics, antidepressants, or anesthetics, which may be, however, inefficient or may have adverse effects, and therefore new treatments are needed. The composition of matter according to the invention mitigated pain in diverse cases, and therefore are believed to be a non-harmful alternative for pain managing. Calcium carbonate finely mixed with organic matter consisting essentially of chitin and polypeptide may hardly present a toxic challenge, when orally administered. Particularly, a gastrolith-derived composition according to the invention, in which the ratio of the organic matter to calcium carbonate in said composition is about 20 wp of the organic matter per 100 wp $CaCO_3$, further containing about 20 wp water and 30 wp inorganic salts, was found to alleviate pain in patients with different diagnostic states, particularly bone pain, when administered at several daily doses (within a week) of about 1-1.5 g (depending on the weight and age of the patient).

In still another aspect of the invention, a composition of matter is provided for treating a bone or bone marrow disorder, including fracture or osteoporosis. The bone formation in humans surpasses or equals bone resorption till the age of about 45 years, followed by a period of the net loss of about 0.5% per year; women may experience up to tenfold higher rate of bone loss during several years after menopause. The patients often suffer from pain in the bones or muscles, fractures may develop. Consumption of 1 to 1.5 g calcium daily is recommended. The composition of matter according to the invention, comprising $CaCO_3$ finely mixed with organic matter, consisting essentially of chitin and polypeptide dispersed in $CaCO_3$, wherein the ratio of the organic matter to calcium carbonate in said composition of from 10 to 30 wp of the organic matter per 100 wp $CaCO_3$ was found to improve the state of patients suffering from osteoporosis. Particularly, a composition originating from crustacean gastrolith, comprising $CaCO_3$ finely mixed with organic matter consisting essentially of chitin and polypeptide, wherein the ratio of the organic matter to calcium carbonate in said composition was about 20 wp of the organic matter per 100 wp $CaCO_3$, and further containing about 20 wp water and about 30 wp inorganic salts, was found to mitigate the osteoporosis symptoms when administered at a daily dose of about 0.5 g; bone loss was stopped, while 1.5 g led to improvements comprising the increase of the bone density measured in the spine. The composition of the invention accelerated healing of bone fractures.

As explained, the invention provides a method of treating a condition selected from the group consisting of proliferative diseases, neurological diseases, bone disorders, and chronic pain, which method comprises administering a therapeutic amount of a composition of matter consisting of calcium carbonate, chitin and polypeptide, wherein the mass ratio of the organic matter to calcium carbonate is from 1/10 to 3/10, and the mass ratio of polypeptide to chitin is from 1/100 to 1/10. Preferably, said composition further comprises water in an amount of up to 30 weight parts and inorganic salts in an amount of up to 40 weight parts per 100 parts of $CaCO_3$. The composition is preferably administered in one dose every day during a period sufficient for achieving an improvement of symptoms or healing of underlying causes associated with said condition. Based on the above findings, the present invention provides a means for treating or mitigating a disorder associated with calcium metabolism, or calcium signaling. The conditions implicated with calcium metabolism or signaling comprise immunologic and proliferative, neurological, cardiovascular and pulmonary, nutritional, musculoskeletal, and dental problems. Said proliferative conditions include cancers; and said treating or mitigating may comprise shrinking a tumor or preventing the proliferation of carcinogenic cells in said tumor. Said neurological conditions include neurodegenerative demyelinating diseases, such as MS, and dementias, such as AD, and movement disorders, such as Parkinson's disease. An advantage of the composition of matter according to the invention is harmlessness of its components, which are a part of natural materials, sometimes even being consumed. The toxicity measurements confirmed the safety of the composition of matter for oral administration. Therapeutic daily doses of from 0.5 g to 2 g of the compositions have been found useful in specific cases, but in view of the low toxicity, the doses may be increased when needed, as a skilled person will appreciate.

The invention relates to a composition of matter, and the use thereof in the preparation of a medicament, mimicking certain features of the composition of crustacean gastrolith, comprising calcium carbonate finely mixed or dispersed with an organic matter which essentially consists of chitin and polypeptide (Pp), wherein the mass ratio (chitin+Pp)/$CaCO_3$ is between 1/10 and 3/10, and the mass ratio Pp/chitin is between 1/100 and 1/10, preferably between 1/100 and 1/20. The composition of the invention may comprise moisture up to about 30 mass parts per 100 mass parts of $CaCO_3$, and it may further comprise inorganic salts other than calcium carbonate up to about 40 mass parts per 100 mass parts of $CaCO_3$. In a preferred embodiment of the invention, said $CaCO_3$ is essentially amorphous. Said other salts may comprise, for example, cations selected from magnesium, potassium, strontium, and sodium, and anions selected from carbonate, phosphate, sulfate, chloride, bromide, and fluoride; the terms anion and cation are used to simply describe the salt composition, without implying anything about the solubility of the salts. If said calcium carbonate is amorphous, the analytical indications, IR and X-ray, as disclosed in WO 2005/115414 are obtained. It is known that some salts, such as phosphates, may support the amorphous state of calcium carbonate. Said composition of the invention may be prepared by homogenizing a mixture containing 100 weight parts of calcium carbonate, and from 10 to 30 weight parts of organic matter consisting essentially of chitin and polypeptide, optionally further including in said mixture up to 30 weight parts of water and up to 40 parts of pharmaceutically acceptable inorganic salts other than $CaCO_3$, wherein said homogenizing achieves fine dispersion of all components, the calcium carbonate preferably appearing as amorphous or microcrystalline. Alternatively, said composition of the invention may be obtained from biological source, for example from crustacean which in certain organs or body parts contain calcium carbonate and said organic matter. Said crustaceans preferably include the order of decapods, represented, for example, by crayfish. Said body part may comprise gastrolith or parts of exoskeleton, preferably of a crayfish, for example Cherax quadricarinatus.

The invention provides a method of preparing a composition of matter comprising calcium carbonate finely mixed or dispersed with an organic matter (Om) which essentially consists of chitin and Pp, comprising i) providing a material containing $CaCO_3$, chitin, and Pp, wherein the mass ratio Om/$CaCO_3$ is between 1/10 and 3/10, and the mass ratio Pp/chitin is between 1/100 and 1/10; optionally adjusting water content in the mixture up to 30 wp per 100 wp $CaCO_3$; optionally adjusting the content of inorganic salts other than $CaCO_3$ in the mixture up to 40 wp per 100 wp of $CaCO_3$; iv) homogenizing the mixture to obtain a fine dispersion. Said homogenizing may comprise stirring, grinding, or milling. Said water adjusting may include drying at higher temperatures or at lower air pressures. In a preferred embodiment, said method of the invention comprises selecting crayfish and monitoring, and optionally inducing, the formation of gastrolith, harvesting developed gastroliths, drying them in hot air, and grinding, thereby to obtain the composition of the invention. In other preferred embodiment, said method of the invention comprises dispersing calcium hydroxide in water, optionally with smaller amounts of sodium and/or potassium phosphate, and saturating the suspension with carbon dioxide while adding chitin and polypeptide, centrifuging the suspension, and drying the sediments with a part of the supernatant, thereby to obtain the composition of the invention. A skilled person can calculate the amounts of the components so as to obtain the desired ratios. Said polypeptide may be selected from soluble and insoluble proteins, acceptable for oral administration.

EXAMPLES

Example 1

Gastroliths of Cherax quadricarinatus were prepared as described [WO 2005/115414]. Dried gastroliths containing about 20 parts of water per 100 parts of $CaCO_3$ were ground to yield a composition of matter according to the invention, denoted CM1 hereinafter. Pharmaceutical formulation according to the invention were obtained by pressing CM1 into tablets according to the methods already described [Ibid].

The toxicity of CM1 was determined on rats (Harlan Biotech Israel, Rehovot). A daily dose of 65 mg CM1 per 1 kg body weight caused no mortality, or any noticeable clinical signs, and all laboratory values were normal during the whole period of 14 days.

Example 2

74 g calcium hydroxide was suspended and stirred in about 250 ml distilled water, carbon dioxide was bubbled into the suspension while adding the following components: 5 g $Na_2HPO_4$, 5 g $KH_2PO_4$, 18 g finely milled crab shell chitin, 4 g BSA. After saturating with $CO_2$, the volume of the suspension was adjusted to 400 ml with water, and the suspension was centrifuged. 200 ml of supernatant was discarded, and the residual volume comprising the sediment was homogenized and dried to reach the moisture of 13% and ground to obtain a composition of matter according to the invention, denoted CM2.

Example 3

Tablets prepared as described in Example 1, containing 0.5 g CM1, were administered to five AD patients. The patients got 0.5-2.0 g daily. The positive response followed within several days, chronic pains decreased within from four to seven days, cognitive abilities and physical activity of the patients increased within about one week.

Example 4

Tablets prepared as described in Example 1, containing 0.5 g CM1, were administered to provide 0.5-2.0 g in one dose to three patients suffering from advanced breast cancers with metastasis in other organs. Positive results related to general feeling and pain were reported after several days, and the state of the patients continued to improve during the whole treatment period, seven months till now. Tumors in the organs have gradually shrunk, reaching less than 50% in lungs, nearly disappearing in bones, and totally disappearing in liver. The bone density increased. In one of the patients, chemotherapy destroyed her nails, and following the treatment according to the invention, the nails started to grow again. Laboratory values, including blood parameters, and calcium, improved. A few days after the start of the treatment, the patients reported a substantial decrease of pain, constipation was observed and treated in two patients.

Example 5

A woman patient suffering from breast cancer, with metastasis in lungs and liver and bones from the time of diagnosis four years ago, had underwent chemotherapy and hormonal therapy which was non-responsive, and was replaced by a monthly treatment with aromasin with aredia a year ago. For several months before starting the treatment with 2 g CM1 daily she had been suffering from cramps in hands and strong pains during the nights, she had been having problems with performing normal home work, objects falling out of her hands. Due to the use of aredia she had exhibited low calcium values (7.1 mg %) even though she had been obtaining calcium additive (Vita Cal). The calcium additive was stopped after starting the treatment with a composition according to the invention.

A month after having started with daily doses of 2 g CM1, the patient has exhibited an improvement in the calcium value (9.3 mg %). The pains and cramps have ceased, her sleep is better, her performance has improved immensely (the first time in three years she has managed to prepare dough, etc.). She is stronger and can walk better, and she does not need pain killers. The last CT test has shown a stabilization in the status of bone and liver growth, and a tendency to an improvement in the breast and lungs growth.

Example 6

Four patients suffering from osteoporosis, age 55-78 years were daily administered tablets of CM1. One patient was receiving a daily dose of 0.5 g during four months with no changes in her situation. Other patient, receiving 1.5 g daily for 5 weeks, showed increase in bone density (the results were compared to the situation 4 years ago before osteoporosis). One patient (72 years old) was receiving 0.8 g daily for 2 months, and 1.5 g daily for 2 months. The bone density measured in the spine increased substantially (up to 13% in several regions of the bone). An improvement in the activity of thyroid gland was reported in one of the patients.

Example 7

Three patients, afflicted with several types of bone fractures comprising pelvis, back and foot (man age 40), leg (age 9), finger (woman age 40) respectively, were administered tablets CM1 for up to two weeks. The finger broken in two regions was treated for a week to a full healing. Pelvis, back and foot fractures in one wounded patient took six weeks to full recovery when taking 1.5 g daily for two weeks from the second week, whereas the initial estimation by the doctors of the recovery time was up to about six months. The patient with a broken leg took 0.5 g CM1 daily and experienced pain reduction within tree days, and full recovery after a week (estimated by the doctors to take three weeks).

Example 8

A woman patient, age 50, having been treated for nearly twenty years with antidepressants, and methadone or related drugs developed kidney problems, and further serious problems with her mandibular bone. After a month treatment with about 1.5 gram dried gastrolith a day, the patient was feeling better, increased her body weight, and stopped using antidepressants and methadone. The state of her mandibular bone substantially improved.

Example 9

Five groups of rats, each consisting of five females, were fed on normal granular food. The animals in groups (1) and (2) were ovarectomized at the age of one month, the animals in group (3) were only incised to open abdomen without ovarectomy—to serve as a control group. After the operation, group (1) received food enriched with 1.2 wt % dried gastrolith, group (2) received food enriched with the corresponding amount of crystalline calcium carbonate, and group (3) received non-enriched food. The animals were sacrificed six weeks after the operation.

The following parameters were checked: total body weight; blood values, including calcium, phosphate, estradiol; mass of femur and tibia after the animals' sacrifice; femur and tibia histology; the mass of femur and tibia ashes (800° C., 12 hours); and Ca and Mg contents in the ashes.

While the body weight was not much affected by different types of treatments among the groups, higher estradiol in the control group ("sham operation") suggested that the ovarectomized animals may serve as an osteoporosis model. The animals obtaining gastrolith in their food showed higher mass of the bones, higher mass of the ashes, and higher contents of both calcium and magnesium in the ashes, when compared with the animals receiving crystalline calcium carbonate.

While this invention has been described in terms of some specific examples, many modifications and variations are possible. It is therefore understood that within the scope of the appended claims, the invention may be realized otherwise than as specifically described.

We claim:

1. A method for treating breast carcinoma comprising orally administering a pharmaceutical composition consisting of
   (A) dried, ground crustacean gastrolith having
      (i) 100 weight parts (wp) of calcium carbonate finely mixed with
      (ii) from 10 to 30 wp of organic matter having
         (a) from 90 to 99 wt % chitin and
         (b) from 1 to 10 wt % polypeptide,
      (iii) up to 30 wp of moisture per 100 wp of calcium carbonate, and
      (iv) up to 40 wp of inorganic salts other than calcium carbonate, and
   (B) a pharmaceutical carrier, a pharmaceutical binding agent, or a pharmaceutical diluent.

2. The method according to claim 1, wherein said inorganic salts are selected from the group consisting of magnesium, potassium, strontium, sodium, phosphate, sulfate, chloride, bromide, and fluoride.

3. The method according to claim 1, wherein the calcium carbonate in said composition is amorphous.

4. The method according to claim 1, wherein said breast carcinoma further comprises metastasis in other organs.

5. The method according to claim 4, wherein said metastasis is bone metastasis.

6. The method according to claim 1, wherein said treating comprises shrinking tumors, stopping their growth, or slowing down or inhibiting the cell proliferation in a tumor.

7. The method according to claim 1, wherein said treating further comprises alleviating pain associated with said breast carcinoma.

8. The method according to claim 1, wherein said composition is administered orally in daily doses of from about 0.5 to about 3 g.

9. The method according to claim 1, wherein said composition is in the form of a tablet.

10. A method for treating breast carcinoma comprising orally administering a pharmaceutical composition consisting of
   (A) dried, ground crustacean gastrolith having
      (i) 100 weight parts (wp) of calcium carbonate finely mixed with
      (ii) from 10 to 30 wp of organic matter having
         (a) from 90 to 99 wt % chitin and
         (b) from 1 to 10 wt % polypeptide,
      (iii) up to 30 wp of moisture per 100 wp of calcium carbonate, and
      (iv) up to 40 wp of inorganic salts other than calcium carbonate.

11. The method according to claim 10, wherein said inorganic salts are selected from the group consisting of magnesium, potassium, strontium, sodium, phosphate, sulfate, chloride, bromide, and fluoride.

12. The method according to claim 10, wherein the calcium carbonate in said composition is amorphous.

13. The method according to claim 10, wherein said breast carcinoma further comprises metastasis in other organs.

14. The method according to claim 13, wherein said metastasis is bone metastasis.

15. The method according to claim 10, wherein said treating comprises shrinking tumors, stopping their growth, or slowing down or inhibiting the cell proliferation in a tumor.

16. The method according to claim 10, wherein said treating further comprises alleviating pain associated with said breast carcinoma.

17. The method according to claim 10, wherein said composition is administered orally in daily doses of from about 0.5 to about 3 g.

18. The method according to claim 10, wherein said composition is in the form of a tablet.

* * * * *